United States Patent

Whitesides et al.

[11] Patent Number: 5,378,813
[45] Date of Patent: Jan. 3, 1995

[54] MESO-2,5-DIMERCAPTO-N,N,N'N'-TETRAMETHYLADIPAMIDE

[75] Inventors: George M. Whitesides, Newton, Mass.; Watson J. Lees, Charlottetown, Canada; Rajeeva Singh, Cambridge, Mass.

[73] Assignee: President and Fellows of Harvard College, Cambridge, Mass.

[21] Appl. No.: 891,565

[22] Filed: May 29, 1992

[51] Int. Cl.$^6$ .......................................... C07C 319/06
[52] U.S. Cl. .................................... 530/404; 530/408; 530/345; 564/154
[58] Field of Search ................ 564/160, 154; 530/408, 530/404, 345

[56] References Cited

U.S. PATENT DOCUMENTS

| | | | |
|---|---|---|---|
| 2,201,929 | 5/1940 | Speakman | 132/204 |
| 2,540,494 | 2/1951 | Schwarz | 132/205 |
| 2,577,711 | 11/1951 | McDonough | 132/201 |
| 2,577,716 | 12/1951 | McDonough | 132/206 |
| 2,736,323 | 2/1956 | McDonough | 132/206 |
| 3,066,077 | 11/1962 | DeMytt et al. | 564/151 |
| 3,768,490 | 10/1973 | Kalopissis et al. | 132/203 |
| 3,790,644 | 2/1974 | Krachock et al. | 132/203 |
| 4,085,217 | 4/1978 | Kalopissis et al. | 514/355 |
| 4,647,655 | 3/1982 | Axén et al. | 546/193 |
| 4,898,726 | 2/1990 | Beste | 132/204 |

OTHER PUBLICATIONS

Jocelyn, 143 *Methods in Enzymology* 246, 1987, "Chemical Reduction of Disulfides".

Cleland, 3 *Biochemistry* 480, 1964, "Dithiothreitol, a New Protective Reagent for SH Groups".

Szajewski and Whitesides, 102 *J. American Chemical Society* 2011, 1980, "Rate Constants and Equilibrium Constants for Thiol-Disulfide Interchange Reactions Involving Oxidized Glutathione".

Houk and Whitesides, 109 *J. American Chemical Society* 6825, 1987, "Structure—Reactivity Relations for Thiol-Disulfide Interchange".

Burns and Whitesides, 112 *J. American Chemical Society* 6296, 1990, "Predicting the Stability of Cyclic Disulfides by Molecular Modeling: Effective Concentrations in Thiol-Disulfide Interchange and the Design of Strongly Reducing Dithiols".

Houk and Whitesides, 45 *Tetrahedron* 91, 1989, "Characterization and Stability of Cyclic Disulfides and Cyclic Dimeric Bis (Disulfides)".

Lees et al., 56 *J. Organic Chemistry* 7328, 1991, "meso-2,5-Dimercapto-N,N,N',N'-tetramethyladipamide: A Readily Available, Kinetically Rapid Reagent for the Reduction of Disulfides in Aqueous Solution".

Treibs and Neumayr, 90 *Chemische Berichte* 76, 1957, "Eine Neue Pyrrolsynthese".

Guha and Sankaran, 3 *Organic Syntheses Collective* 623, "Muconic Acid" 1956.

*Primary Examiner*—Allen J. Robinson
*Assistant Examiner*—Brian M. Burn
*Attorney, Agent, or Firm*—Lyon & Lyon

[57] ABSTRACT meso-DTA and method for its use in reducing disulfide bonds.

3 Claims, No Drawings

MESO-2,5-DIMERCAPTO-N,N,N'N'-TETRAMETHYLADIPAMIDE

This invention was supported under Grant No. GM30367, and the U.S. Government may have certain rights to the invention.

BACKGROUND OF THE INVENTION

This invention relates to chemicals useful for disulfide reduction.

Jocylin, 143 *Method in Enzymology* 246, 1987 describes disulfide reductions by dithiothreitol (DTT) and dithioerythritol (DTE). It also describes use of mercaptoethanol and other agents for reduction of disulfides.

Cleland, 3 *Biochemistry* 480, 1964 describes the utility of DTT in maintaining monothiols in a completely reduced state.

Szajewski and Whitesides, 102 *Journal American Chemical Society* 2011, 1980 describe rate constants and equilibrium constants for thiol disulfide interchange reactions.

Houk and Whitesides, 109 *Journal American Chemical Society* 6825, 1987 describe the structure reactivity relations for thiol disulfide exchange.

Burns and Whitesides, 112 *Journal American Chemical Society* 6296, 1990 describe methods for protecting stability of cyclic disulfide.

Houk and Whitesides, 45 *Tetrahedron* 91, 1989 describe the characterization of stability of cyclic disulfides.

Axen et al., U.S. Pat. No. 4,647,655 describe a method for splitting disulfide bonds.

Kalopissis, U.S. Pat. Nos. 4,085,217, McDonough, 2,736,323, Brown et al., 2,847,351, McDonough, 2,577,7121, Schwarz, 2,540,494, Speakman, 2,201,929, McDonough, 2,577,710, De Mytt et al., 3,066,077, Beste, 4,898,726, and Kalopissis et al., 3,768,490 generally describe agents useful as cosmetics or for setting of hair which include use of one or more disulfide reducing agents.

SUMMARY OF THE INVENTION

The novel chemical meso-2,5-dimercapto-N,N,N',N'-tetramethyladipamide (meso-DTA) has been discovered to reduce disulfide bonds up to 8 times faster (kinetic) than does dithiothreitol (DTT) in aqueous solution at pH 7.0. meso-DTA, which forms a cyclic disulfide, is less reducing than DTT by approximately 56 mV, but is much more reducing than mercaptoethanol. meso-DTA is easily synthesized in five steps (39% overall yield) from adipic acid.

Thus, in various aspects, the invention features meso-DTA and methods for its use in reducing disulfide bonds. The invention also features methods for forming meso-DTA.

DESCRIPTION OF THE PREFERRED EMBODIMENTS

Disulfide Reducing Agents

This invention features reduction of small organic disulfides and protein disulfides in water at pH 7.0 using meso-2,5-dimercapto-N,N,N',N'-tetramethyladipamide (meso-DTA).

Disulfide-reducing reagents are used in biochemistry to inhibit the oxidation of thiol groups and to reduce disulfide groups in proteins. Jocelyn, Methods Enzymol. 1987, 143, 246–256; Gilbert, Adv. Enzymol. 1990, 63, 69–172; Jocelyn, Biochemistry of the SH Group; Academic: London, 1972; and Huxtable, Biochemistry of Sulfur; Plenum: New York, 1986. A useful thiol reducing reagent for disulfides should have $pK_a \sim 7.0$ for the SH group, a high reduction potential, ready availability, an unobjectionable odor, high solubility in water, kinetic stability at room temperature, and low toxicity. Cleland, Biochemistry 1964, 3, 480–482; and Whitesides, et al., J. Org. Chem. 1977, 42, 332–338.

N,N'-dimethyl-N,N'-bis(mercaptoacetyl) hydrazine (DMH), (Singh and Whitesides, J. Org. Chem. 1991, 56, 2332–2337) is a reagent that reduces disulfides faster than dithiothreitol (DTT), (Cleland, Biochemistry 1964, 3, 480–482) but is more expensive to synthesize. Mercaptoethanol (ME) and dithiothreitol (DTT) are the most commonly used disulfide-reducing reagents in biochemistry. (Jocelyn, P. C. Methods Enzymol. 1987, 143, 246–256.) The principal advantage of ME is its low cost. ME has, however, the disadvantage of a low reduction potential and a relatively high $pK_a$, 9.6. The primary advantage of DTT is that it is strongly reducing. DTT also has several disadvantages: oxidation of DTT by $O_2$ in the presence of transition-metal ions can generate hydrogen peroxide (Trotta et al., J. Biol. Chem. 1974, 249, 1915–1921 and Costa et al., Biochem. Biophys. Res. Commun. 1977, 78, 596–603); it is a strong chelating agent and can sequester essential ions (especially transition metals); it is not a fast reductant (the lower $pK_a$ of the thiol groups in DTT is 9.2 (Szajewski and Whitesides, J. Am. Chem. Soc. 1980, 102, 2011–2026), thus only about 1% of DTT exists as the thiolate at pH 7.0); and it is expensive. (For nomenclature, we indicate the oxidized form of a thiol, the disulfide, by the superscript "ox" and leave the reduced form, the thiol, unsuperscripted: e.g., DTT (dithiol) vs. $DTT^{ox}$ (disulfide).)

meso-DTA meso-DTA was synthesized in 39% overall yield on a 100-mmol scale according to Scheme I

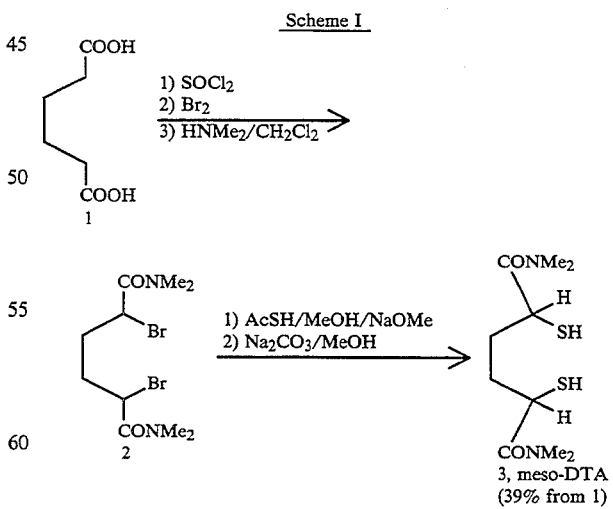

The only purification step (excluding extractions) is the final recrystallization. The bromination of adipoyl chloride leads to two products in a 1.6:1.0 ratio (probably meso:dl isomer; see below) as determined by integration of the ¹H NMR spectrum. Addition of dimethylamine to the crude mixture results in two products, 2, again in about a 1.6:1.0 ratio. If 2 is recrystallized, then only one product (probably meso; see below) is obtained in greater than 50% overall yield based on 1. Reaction of crude 2 (1.6:1.0) with thiolacetic acid and sodium methoxide in methanol at reflux produces only one stereoisomer, in high yield. We believe that the production of only one stereoisomer reflects isomerization under the reaction conditions. Deacetylation of the thiolacetate produces only one stereoisomer, meso-DTA. Oxidation of the dithiol, meso-DTA, to the disulfide, meso-DTA$^{OX}$, and subsequent analysis of the $^1$H NMR coupling constants at 20° and −60° C. established that the dithiol was the meso isomer. The dl isomer of DTA (dl-DTA) could be isolated as a minor product by following a similar route except that the addition of thiolacetic acid and sodium methoxide to crude 2 as performed at 0° C. Isolation of the dl isomer required several chromatographic steps.

Referring to Table 1, the rates of reduction of various disulfides with meso-DTA and DTT were compared. meso-DTA reduces the disulfide linkage of small organic disulfides and dipeptides 5–8 times faster than DTT in water at pH 7.0, and the disulfide bond in proteins 2–5 times faster. In papain and creatine kinase, the disulfide being reduced is derived from an essential active site cysteine, (Smith et al., Biochemistry 1975, 14, 766–771) and the rate measured is the rate of reactivation of the modified protein. (Shaked et al., Biochemistry 1980, 19, 4156–4166.) DNase is deactivated by the reduction of an internal disulfide. (Shaked et al., Biochemistry 1980, 19, 4156–4166; and Price et al., J. Biol. Chem. 1969, 244, 929–932.)

TABLE I

Rates of Reduction of Disulfides with meso-DTA and DTT

| disulfide | $k_{app}^{DTAa}$ $M^{-1}g^{-1}$ | $k_{app}^{DTTa}$ $M^{-1}g^{-1}$ | $k_{app}^{DTA}/k_{app}^{DTT}$ | $k_{app}^{DTA}/k_{app}^{DMHb}$ |
|---|---|---|---|---|
| mercaptoethanol disulfide | 0.50 | 0.065 | 7.7 | 1.1 |
| glutathione disulfide | 0.31 | 0.056 | 5.5 | |
| papain-S-S-Me | 260 | 58 | 4.5 | 0.15 |
| creatine kinase-S-S-glutathione | 78 | 23 | 3.4 | 0.5 |
| DNase | 0.34 | 0.19 | 1.8 | 0.4 |

[a]The rate constants are for aqueous solutions at pH 7.0 and 298 K.
[b]Data taken from Singh and Whitesides, J. Org. Chem. 1991, 56, 2332–2337.

Referring to Table II, meso-DTA completely reduces noncyclic disulfides (mercaptoethanol disulfide or glutathione disulfide) as determined by $^1$H NMR spectroscopy. meso-DTA only partially reduces DTT$^{OX}$ in 50 mM phosphate buffer at pD 7.0 ($K_{eq}=$[meso-DTA$^{OX}$][DTT]/[meso-DTA][DTT$^{OX}$]$=0.010$). dl-DTA is more reducing than meso-DTA by a factor of 10 in 100 mM phosphate buffer at pD 7.0 ($K_{eq}=$[meso-DTA$^{OX}$][dl-DTA]/[meso-DTA][dl-DTA$^{OX}$]$=0.10$). We used the equilibrium constant between meso-DTA and DTT to determine the values of $\epsilon°$ and K(ME) of meso-DTA. Some other useful physical properties of meso-DTA, DTT, and DMH are listed in Table II.

TABLE II

Physical Properties of DTA, DTT and DMH[a]

| physical property | meso-DTA | dl-DTA | DTT | DMH |
|---|---|---|---|---|
| $\epsilon^{a,b}$V | −0.300 | −0.328 | −0.356 | −0.300 |
| p$K_a$ | 7.8, 8.9 | | 9.2, 10.1 | 7.6, 8.9 |
| mp,[a] °C | 118 (137) | | 42 (132) | 38 (155) |
| $k_{app}^c$ $M^{-1}g^{-1}$ | 0.50 | | 0.065 | 0.52 |
| K,[d] M | $10^3$ | $10^4$ | $10^5$ | $10^3$ |
| solubility,[a,c] mM | 80 (80) | | high | 250 (23) |
| odor[a] | weak (none) | | weak (none) | weak (none) |

[a]Data in parentheses are for the oxidized form containing a disulfide group.
[b]All values of $\epsilon°$ are relative to mercaptoethanol (−0.209 V).
[c]The apparent rate constant ($k_{app}$) is for the reduction of mercaptoethanol disulfide (ME$^{OX}$) at pH 7.0 in aqueous phosphate buffer (50 mM).
[d]The values of equilibrium constant (K) are for the reduction of ME$^{OX}$ with the dithiol in water, pH 7.0, 100 mM phosphate buffer, $K_{eq}=$ ([ME$^{red}$]$^2$[cyclic disulfide]/[ME$^{OX}$][dithiol]).
[e]The solubilities were determined in phosphate buffer (pH 7.0, 100 mM phosphate, 25° C).

The p$K_a$ of the first thiol in meso-DTA is 7.8±0.2, therefore, at pH 7.0 approximately 15% of meso-DTA exists as the thiolate. On the basis of this p$K_a$, we calculate (Szajewski et al., J. Am. Chem. Soc. 1980, 102, 2011–2026) that meso-DTA should reduce disulfides 4.4 times faster than DTT at pH 7.0. (Using the Bronsted equation log k=7.0+0.5 p$K_a^{nuc}$−0.27 p$K_a^c$−0.73 p$K_a^{lg}$ and the equation k=k$^{app}$ (1 + 10$^{pKa-pH}$), we calculate $k_{app}^{meso-DTA}/k_{app}^{DTT}=4.4$.) The relative rate of reduction of disulfides by meso-DTA compared to DTT is approximately 6 for small peptides and small organic disulfides (Table I), a value that is slightly above that calculated. For proteins, the relative rate of meso-DTA vs. DTT (2–5-fold faster) is less than or equal to the calculated value (4.4-fold faster). The difference between the calculated and the actual value for proteins could be due to steric interactions, because meso-DTA is a secondary thiol and DTT is a primary thiol. The difference in rates could also be due to the relative difference in hydrophobicities of the two compounds.

The equilibrium constant for reduction of ME$^{OX}$ by meso-DTA is less than that of DTT by a factor of $10^2$ probably due to the 1,3-diaxial interaction in meso-DTA$^{OX}$. In the meso-DTA$^{OX}$, the 1,3-diaxial interaction between the axial hydrogen and axial dimethylamido group will be destabilize the cyclic disulfide (meso-DTA$^{OX}$) relative to the noncyclic dithiol (meso-DTA). This inference is supported by the fact that dl-DTA is 10 times more reducing than meso-DTA. In DTT$^{OX}$ there are no 1,3-diaxial interactions to destabilize the oxidized form relative to the unoxidized form (DTT).

meso-DTA and DMH have similar reduction potentials and p$K_a$'s, but DMH reduces hindered disulfides more rapidly than does meso-DTA. This increased rate of reduction of hindered disulfides is probably due to differences in steric interactions and hydrophobicities since DMH contains a primary thiol while meso-DTA contains a secondary thiol.

meso-DTA is less soluble in water than DTT. Since nearly all applications in protein chemistry require a concentration of reducing agent less than 50 mM, the lower solubility of meso-DTA should not be disadvantageous. In fact, the lower solubility of meso-DTA in water permits its extraction from water with organic solvents.

We believe that for most applications meso-DTA is superior to or equal to DTT. ME is inexpensive, but weakly reducing and kinetically slow. DTT is strongly reducing but is reasonably expensive and kinetically slow. DMH is strongly reducing and kinetically fast, but is expensive to synthesize (primarily because 1,2-dimethylhydrazine, the starting material, is expensive). meso-DTA is strongly reducing, relatively inexpensive to synthesize, and kinetically fast.

METHODS

The following examples are described in Lees et al., 56 *J. Org. Chem.* 7328, 1991 hereby incorporatd by reference herein. These examples provide one method for formation of meso-DTA, and show how the results in Tables I and II were obtained. Starting materials were commercial products: Thionyl chloride, bromine, and thiolacetic acid (Fluka): dimethylamine and adipic acid (Aldrich); papain (Boehringer Mannheim); creatine phosphokinase, deoxyribonuclease I, DNA, and N-benzoyl-L-arginine p-nitroanilide (Sigma). NMR spectra were recorded in $CDCl_3$. Chemical shifts are reported in δ (ppm) using $CHCl_3$ (7.24) as an internal standard. Elemental analyses were performed by Oneida Research Services.

Example 1 meso-2,5-Dimercapto-N,N,N',N'-tetramethyladipamide (meso-DTA)(3)

The procedure of Treibs and Neumayr, Chem. Ber. 1957, 90, 76–79.) was generally followed. Specifically, adipic acid (1,832 mmol, 120.0 g) and thionyl chloride (2.33 mil, 170 mL) were heated at reflux for 90 min with no solvent in a three-necked 1-L flask equipped with a reflux condenser and an addition funnel. The exhaust gases from the reflux condenser were neutralized by bubbling through a 5M NaOH solution. The $^{13}C$ NMR (75 MHz) spectrum of the resulting oil showed peaks at δ173.1, 46.2, and 23.5. Bromine (1.88 mol, 97 mL) was added over 5 h at 95° C. and the reaction mixture kept at 95° C. for another 4 h before being cooled at 25° C. The $^1H$ NMR spectrum of the product showed two major components: meso- and dl-2,5 dibromoadipoyl chloride in a 1.6:1.0 ratio. The solution was dissolved in $CH_2Cl_2$ (70 mL) and added over 2 h to a biphasic mixture of $CH_2Cl_2$ (1 L) and dimethylamine (600 mL of a 40% w/w aqueous solution) in a 3-L flask cooled by an ice/salt bath. The temperature of the reaction mixture was kept at 18° C. or less. The resulting biphasic mixture was acidified to pH 4.0 with concentrated hydrochloric acid (ca. 20 mL). The organic layer was separated and extracted with saturated aqueous sodium bicarbonate (150 mL), dried with $MgSO_4$, and concentrated under aspirator pressure to provide 197 g of a crude mixture of meso and dl product 2 (1.6:1.0 ratio). A small portion (ca. 50 mg) was separated by chromatography on silica gel (eluant: 1:1 ethyl acetate/hexane going to ethyl acetate. The crude product was divided into two portions: 97.5 g and 100 g.

The first portion was recrystallized from $CH_2Cl_2$ (ca. 500 mL) and ether (ca. 500 mL) to provide 74.8 g (51% overall yield) of a single diastereomer 3 (which we presume to be the meso isomer; see below). A second recrystallization from a mixture of ether (200 mL) and $CH_2Cl_2$ (100 mL) produced 14.0 g of a mixture of meso and dl product (5:1 ratio, the major product being the same as the product from the first recrystallization).

The second portion of crude dibromide mentioned above (279 mmol, 100 g) and thiolacetic acid (923 mmol, 66 mL) were dissolved in methanol (500 mL). Sodium methoxide (700 mmol, 37.8 g) was added at a rate that maintained reflux (over 30 min). The solution was stirred for 1 h as it cooled to 25° C. The solution was concentrated under aspirator pressure and partitioned between $CH_2Cl_2$ (500 mL) and 300 mL of 5% aqueous sodium bicarbonate solution. The organic layer was separated, and the aqueous layer was extracted with $CH_2Cl_2$ (2×100 mL). The combined organic layers were dried ($MgSO_4$) and concentrated under aspirator pressure to provide a crude yellow solid (the diacetate of meso-DTA; 99.6 g). Only one stereoisomer was observed by $^1H$ NMR.

The yellow solid and potassium carbonate (655 mmol, 90.5 g) were added to methanol (400 mL) that had been purged with argon. The mixture was stirred for 14 h under argon, $CH_2Cl_2$ (200 mL) was added and the solution acidified to pH 3.0 with concentrated sulfuric acid (ca. 35 mL) over 1 h. The solution was partitioned between ethyl acetate (1000 mL) and water (600 mL). The layers were separated, and the water layer was extracted with ethyl acetate (2×300 mL). The combined organic layers were dried ($MgSO_4$) and concentrated under reduced pressure to provide 77.6 g of crude product, which was recrystallized from tetrahydrofluorine (THF) (ca. 100 mL) to provide 37.9 g of meso-DTA. The mother liquor was dissolved in $CH_2Cl_2$ (200 mL) and extracted with 100 mL of 0.2N HCl. The organic layer was concentrated in vacuo, and crystallized from THF to provide a further 5.7 g of meso-DTA (39% total overall yield from adipic acid).

Example 2

Oxidized meso-DTA

Ellman's reagent (2.0 g, 6.45 mmol) was added to water 75 (mL), and the pH was adjusted to 7.0 with saturated aqueous $NaHCO_3$ solution. meso-DTA (1.03 g, 3.89 mmol) was added, and the solution was stirred for 15 min. $CH_2Cl_2$ (25 mL) was added, and the layers were separated. The water layer was back-extracted with $CH_2Cl_2$ (2×50 mL). The combined organics were dried ($MgSO_4$) and concentrated at aspirator pressure to provide 981 mg (96%) of product.

Example 3 dl-DTA

The product of the secondary recrystallization of 2 (5:1 ratio of meso to dl 2.50 g) was chromatographed on silica gel (ethyl acetate/hexane, 3:1 going to 5:1) to provide 448 mg of a 1:1 (meso:dl) mixture. This mixture was dissolved in 30 mL of methanol and cooled to 0° C. Sodium methoxide (160 mg) and thiolacetic acid (300 μL) were added. After 15 min at 0° C., the solution was warmed to room temperature, concentrated in vacuo, and partitioned between water (10 mL) and $CH_2Cl_2$ (20 mL). The organic layer was dried ($MgSO_4$), concentrated in vacuo, and chromatographed on silica gel (ethyl acetate going to ethyl acetate/methanol, 10:1) to provide 169 mg of the dl-dithiolacetate of DTA. The dl-dithiolacetate of DTA was dissolved in 10 mL of methanol. After addition of sodium methoxide (48 mg), the solution was stirred for 20 min, acidified with DOWEX 50X8 ion-exchange resin (H+ form), filtered, and partially concentrated under aspirator pressure (2 mL). The methanolic solution was added to an aqueous solution of Ellman's reagent (210 mg, adjusted to pH 7.0 with saturated $NaHCO_3$). After 10 min, the solution was extracted with CH$_2$Cl$_2$ (2×20 mL). The combined organics were dried (MgSO$_4$), concentrated under aspirator pressure, and chromatographed on silica gel (ethyl acetate going to ethyl acetate/methanol, 10:1) to provide 58 mg of dl-DTA$^{OX}$.

Example 4

Equilibration of dl-DTA and meso-DTA dl-DTA$^{OX}$ (2 mg in 0.5 mL of buffered D$_2$O (100 mM NaPO$_4$, pD 7.0)) and meso-DTA (6 mg in 1.5 mL of buffered D$_2$O (100 mM NaPO$_4$, pD 7.0)) were mixed in an NMR tube, and $^1$H NMR spectra were taken at various times. The value of K$_{eq}$ was calculated from the $^1$H NMR integrals.

Example 5

Determination of the pK$_a$ of meso-DTA

The absorbance at 238 nm of meso-DTA (100 μL of an 8 mM ethanolic solution of meso-DTA) in various aqueous buffers (3 mL, 50 mM: 2,2-dimethylsuccinate, pH 6.0, 6.4, 6.8; Tris, pH 7.0, 7.3, 7.7, 8.0, 8.3, 8.7; glycine, pH 9.0, 9.5, 10.0) was plotted against pH. This curve was then compared with plots derived from theory. The best fit was obtained when the first pK$_a$ was 7.8±0.2 and the second was 8.9±0.2.

Example 6

Kinetics of Reduction of Glutathione Disulfide by meso-DTA and DTT Using $^1$H NMR Spectroscopy The following solutions were prepared using a 50 mM phosphate buffer solution (pD 7.0 in D$_2$O) that had been deoxygenated by bubbling argon through it for 30 min: 10 mM glutathione disulfide solution (15.9 mg in 1.5 mL of buffer); 10 mM DTT solution (3.1 mg in 2 mL of buffer); 10 mM meso-DTA solution (5.3 mg in 2 mL of buffer). Three NMR tubes containing 250 μL of the DTT solution and 250 μL of the glutathione disulfide solution were prepared. The thiol-disulfide interchange reaction was quenched by addition of 25 μL of a DCl solution (12 wt % in D$_2$O) in one tube after 2 min, in another tube after 4 min, and in another tube after 6 min. The same series of experiments was carried out with the meso-DTA solution instead of the DTT solution. The second-order rate constant was calculated from the integrals of the $^1$H NMR spectra. A similar procedure was used for studying the kinetics of reduction of mercaptoethanol disulfide by meso-DTA and DTT.

Example 7

Equilibrium Experiments

A 10 mM DTT$^{OX}$ solution (3.0 mg in 2.0 mL of buffer) and a 10 mM meso-DTA solution 5.3 mg in 2 mL of buffer) were made up in D$_2$O buffer (50 mM phosphate, pD 7.0). The DTT$^{OX}$ solution (250 μL) and the meso-DTA solution (250 μL) were mixed in an NMR tube. After 4 h, a $^1$H NMR spectrum was obtained. The equilibrium constant between meso-DTA and DTT was calculated using the integrals obtained from the $^1$H NMR spectrum. When meso-DTA was equilibrated with a 1.5-fold excess of mercaptoethanol disulfide (6 mM) of glutathione disulfide (6 mM), meso-DTA was oxidized completely, and no mixed disulfide or reduced was observed by $^1$H NMR spectroscopy.

Example 8

Kinetics of Reactivation of Creatine Kinase-S-S-Glutathione

The solution of creatine kinase S-S-glutathione (the procedure was analogous to that of Walters and Gilbert, J. Biol. Chem. 1986, 261, 15372–15377) (10 μL) was diluted with deoxygenated aqueous buffer (pH 7.0, 0.1M imidazole, 2 mM EDTA, 2.5 mL). The diluted solution was added to two flasks (1.0 mL each). DTT or meso-DTA (5 μL of a 5 mM solution in pH 6.0 aqueous imidazole buffer) was added to the flask containing enzyme (t=0). At various times, a 50-μL aliquot was withdrawn and added to an assay solution (950 μL, pH 6.0, 0.1M imidazole, 2 mM EDTA, 10 mM MgCl$_2$, 2 mM ADP, 20 mM d-glucose, 2 mM NADP, 30 mM phosphocreatine, hexokinase (50 units/mL), glucose-6-phosphate dehydrogenase (35 units/mL)). The rate of increase in absorbance at 340 nm was recorded. (Gerhardt, Methods of Enzymatic Analysis, 3rd ed.; Bergmeyer, Ed.; Verlag Chemie: Weinheim, 1983; Vol. III, pp. 508–524.)

Example 9

Kinetics of Reactivation of Papain-S-S-Me

The papain-S-S-Me was prepared as described by Shaked et al., Biochemistry 1980, 19, 4156–4166. To assay (Mole and Horton, Biochemistry 1973, 12, 816–822) for the rate of reactivation of papain disulfide with DTT and meso-DTA, we used a procedure similar to that described in Singh and Whitesides, J. Org. Chem. 1991, 56, 2332–2337.

USES meso-DTA is useful in many reactions in place of the above-described reducing agents, especially DTT. Those of ordinary skill in the art will recognize that meso-DTA may simply be substituted for DTT but may be used in lower amounts, or for shorter time periods in standard reducing reactions.

Other embodiments are within the following claims.

We claim:

1. Method for reducing disulfide bonds in a biochemical reaction by contacting a chemical comprising said bonds with meso-DTA under disulfide bond reducing conditions.

2. The method of claim 1, wherein said chemical is a protein comprising a disulfide bond.

3. The method of claim 1, wherein said chemical is selected from the group consisting of mercaptoethanol disulfide, glutathione disulfide, papain-S-S-Me, creatine kinase-S-S-glutathione, and DNase.

* * * * *